United States Patent
Herges et al.

(10) Patent No.: US 9,786,420 B2
(45) Date of Patent: Oct. 10, 2017

(54) MOLECULAR SWITCH

(75) Inventors: Rainer Herges, Kronshagen (DE); Olav Jansen, Strande (DE); Felix Tuczek, Kiel (DE); Sugumar Venkataramani, Kiel (DE)

(73) Assignees: Christian-Albrechts-Universität zu Kiel, Kiel (DE); Universitätsklinikum Schleswig-Holstein, Kiel (DE)

( * ) Notice: Subject to any disclaimer, the term of this patent is extended or adjusted under 35 U.S.C. 154(b) by 1240 days.

(21) Appl. No.: 13/817,368

(22) PCT Filed: Aug. 10, 2011

(86) PCT No.: PCT/DE2011/001573
§ 371 (c)(1),
(2), (4) Date: Apr. 16, 2013

(87) PCT Pub. No.: WO2012/022299
PCT Pub. Date: Feb. 23, 2012

(65) Prior Publication Data
US 2013/0202538 A1 Aug. 8, 2013

(30) Foreign Application Priority Data

Aug. 16, 2010 (DE) .................. 10 2010 034 496

(51) Int. Cl.
| | | |
|---|---|---|
| H01F 1/42 | (2006.01) | |
| A61K 31/40 | (2006.01) | |
| C07F 15/04 | (2006.01) | |
| C09K 9/02 | (2006.01) | |
| A61K 49/10 | (2006.01) | |
| A61K 31/409 | (2006.01) | |

(52) U.S. Cl.
CPC ............. *H01F 1/42* (2013.01); *A61K 31/409* (2013.01); *A61K 49/101* (2013.01); *C07F 15/045* (2013.01); *C09K 9/02* (2013.01); *C09K 2211/1007* (2013.01); *C09K 2211/1014* (2013.01); *C09K 2211/1029* (2013.01); *C09K 2211/187* (2013.01)

(58) Field of Classification Search
CPC ...... A61K 31/409; A61K 49/101; C09K 9/02; C09K 2211/1007; C09K 2211/1029; C09K 2211/187; C09K 2211/1014; H01F 1/42; C07F 15/045
See application file for complete search history.

(56) References Cited

U.S. PATENT DOCUMENTS

| | | | | |
|---|---|---|---|---|
| 5,980,862 A | * | 11/1999 | Meade ................. | A61K 49/085 424/1.11 |
| 2004/0230044 A1 | * | 11/2004 | Louie ................... | A61K 49/085 534/16 |

FOREIGN PATENT DOCUMENTS

DE 10039903 A1 2/2002

OTHER PUBLICATIONS

Kume et al., Dalton Trans., 2008, 3260-3271.*
Guerchais et al., Coordination Chemistry Reviews, 2010, 254, p. 2533-2545.*
Kano et al., JACS, 2006, 128, p. 7097-7109.*
Yutaka et al., Inorg. Chem., 2003, 42, p. 6306-6313.*
Shinkai et al., J. Am. Chem. Soc., 1980, 102, 5860-5865.*
Kimura et al., Analyst, 2000, 125, p. 1091-1095.*
Hasegawa et al., Dalton Trans., 2009, p. 280-284.*
Boillot, M-L. et al., "First Ligand-Driven Light-Induced Spin Change at Room Temperature in a Transition-metal Molecular Compound," Jan. 1999, *New Journal of Chemistry*, vol. 23, No. 2, p. 179-183, Royal Society of Chemistry.
Bornholdt, C., "Ligandgetriebener lichtinduzierter Spin-Crossover in Einzelmolekülen bei Raumtemperatur," 2008, XP002667555, p. 1-270, Christian-Albrechts-Universität.
Matino, F. et al., "Single azopyridine-substituded porphyrin molecules for configurational and electronic switching," Sep. 2010, *Chemical Communications*, vol. 46, Numer 36, p. 6780-6782.
Sour, A. et al., "First Evidence of a Photoinduced Spin Change in an FEIII Complex Using Visible Light at Room Temperature," Nov. 15, 1999, *European Journal of Inorganic Chemistry*, vol. 12, p. 2117-2119.

* cited by examiner

*Primary Examiner* — Michael G Hartley
*Assistant Examiner* — Leah Schlientz
(74) *Attorney, Agent, or Firm* — Saliwanchik, Lloyd & Eisenschenk (57) ABSTRACT

Photosensitive molecular switch, having a chelate ligand, a metal ion bonded coordinatively to the chelate ligand, the metal ion being selected from the group of metal ions consisting of $Mn^{2+}$, $Mn^{3+}$, $Fe^{2+}$, $Fe^{3+}$, $Co^{2+}$ and $Ni^{2+}$, a photochromic system which is bonded covalently to the chelate ligand and can be isomerized by irradiation, this system being bonded coordinatively to the metal ion in one configuration and not bonded to the metal ion in the other configuration.

14 Claims, 5 Drawing Sheets

MOLECULAR SWITCH

CROSS REFERENCE TO A RELATED APPLICATION

This application is a National Stage Application of International Application Number PCT/DE2011/001573, filed Aug. 10, 2011; which claims priority to German Patent Application No. DE 10 2010 034 496.6, filed Aug. 16, 2010; all of which are incorporated herein by reference in their entirety.

The present invention relates to a photosensitive molecular switch.

In particular, the present invention relates to transition metal complexes having a special ligand system that enables a change of the magnetic spin states, the preparation thereof and the use thereof in applications such as contrast agents for magnetic resonance imaging, optical storage media and for the contact-free manipulation of objects.

U.S. 2007/0218010A1 and EP 2 053 049 A1 disclose contrast agents for magnetic resonance imaging comprising ligands that allow changing the spin state of the central atom. Modifications of the coordination sphere by enzymatic cleavage of ligands (U.S. 2007/0218010A1) or variations of the temperature (EP 2 053 049 A1) or of the pH may cause a change of the magnetic state (spin crossover, SCO) and thus a change of the effect as contrast agent.

Generally, the procedure is to inject the contrast agent first, which then is dispersed via the blood circulation in the whole body. The contrast effect is based on the fact that the agent is more soluble in water than in fat, which means that it primarily accumulates in blood and less so in fat tissue. The result is a very good imaging for blood vessels. This method is called magnetic resonance angiography (MRA).

For many applications such as the examination of circulatory disorders, and particularly for imaging of the coronary blood vessels of patients with infarction, angiography has the major disadvantages that the MRI scanner is not quick enough for imaging the coronary blood vessels, which are in continuous motion, and that it is impossible to show the dynamics of the blood flow. The latter is particularly important when examining patients with cerebral infarction or other neurological diseases.

In an inhomogeneous magnetic field, diamagnetic substances (most substances of relevance for engineering, environment and nature are diamagnetic) are subjected to a force pointing in the direction of the decreasing magnetic field (see also Gouy balance for measuring the diamagnetic susceptibility). It is also known, that the force affecting the diamagnetic sample not only depends on the strength of the magnetic field gradient and the diamagnetic susceptibility of the sample, but also on the magnetic susceptibility of the vicinity of the diamagnetic sample. The force is proportional to the difference of the magnetic susceptibility of the sample and the vicinity. Due to similarities to buoyancy, this principle is also called magnetic Archimedes' principle.

Using the magnetic Archimedes' principle is currently limited by the fact that the forces acting on diamagnetic objects can only be controlled by changing the outer magnetic field gradient. Thus, a targeted, selective manipulation of single objects within the magnetic field is only possible to a limited extent. This could be achieved by a specific change of the magnetic susceptibility of the medium, in which the object is present, with a high spatial resolution. To date, such a change has been achieved only in solids (and even there only to a limited extent). However, objects obviously cannot move freely in solids.

From the dissertation "Ligandgetriebener lichtinduzierter Spin-Crossover in Einzelmolekalen bei Raumtemperatur" by C. Bornholdt (Ligand-driven, light-induced spin crossover in single molecules at room temperature, 2008), light-switchable complexes are known that can change from the low spin state into the high spin state at 365 nm (UV range). The paramagnetic high spin state of these complexes is stable only at low temperatures and in the solid state, not in solution.

Photoswitchable single molecule magnets are mainly applied for information storage. Here, the great potential of these compounds is their high storage capacity (S. Kawata, Y. Kawata, Chem. Rev. 2000, 100, 1777).

The capacity to induce spin crossover of a transition metal complex by irradiation with light is called LIESST (Light-Induced Excited Spin-State Trapping). The LIESST effect at room temperature is only observed in solids.

Known SCO compounds (generally based on Fe(II) or Fe(III)) can be switched from low spin to high spin by light; however, the paramagnetic high spin state in an isolated molecule is only long lasting at very low temperatures (<50 K). The high spin state returns very quickly to the low spin state (being inactive as contrast agent) which is thermodynamically more stable.

The problem of the invention is to provide a photosensitive molecular switch that can be switched from one magnetic state into the other under the influence of light, and that is stable at room temperature even in the thermodynamically less stable (usually paramagnetic) state. In particular, the problem is to provide a molecular switch that is suitable as contrast agent for magnetic resonance imaging.

The objective is achieved by the compounds described in the claims. The dependent claims disclose the particular embodiments of the invention.

The present invention provides transition metal complexes that can be switched from one magnetic state into the other by means of light, and that are stable even at room temperature in solution in both the high spin and the low spin state.

The present invention provides transition metal complexes that can be switched from one magnetic state into the other by means of light having a physiologically well acceptable wave-length, i.e. in the visible range, and that are stable even in the paramagnetic state at room temperature.

The invention allows the specific change of the magnetic susceptibility of a solution with high spatial resolution and thus effecting a contact-free, light-controlled manipulation of objects in the solution in an inhomogeneous magnetic field.

Finally, the invention provides a photosensitive molecular switch for the formation of storage media.

It was found, that the first LD-CISCO (light-driven coordination-induced spin crossover) complexes stable in a paramagnetic state and in solution are obtained by using a switchable transition metal complex consisting of a transition metal ion, a chelate ligand with one or more substituents, a photochromic system, an axial ligand and a bridge. Wherein the transition metal ion is selected from the group of $Mn^{2+}$, $Mn^{3+}$, $Fe^{2+}$, $Fe^{3+}$, $Co^{2+}$ and $Ni^{2+}$, and the chelate ligand is designed so that it causes the formation of complexes with an approximately square planar (e.g. for $Ni^{2+}$) or approximately square pyramidal (e.g. for $FP^{2+}$) configuration, and the one or more substituents are so that already changing the coordination number by one (e.g. from 4-fold to 5-fold coordination or from 5-fold to 6-fold coordination) provokes a change of the spin state), and the photochromic system isomerizes on irradiation with light, and the axial ligand is electron-rich, and the bridge for covalently attaching the switch to the complex is designed so that the axial ligand is positioned in one of the two configurations exactly in the middle, 1.8-2.4 Å above the transition metal ion, and the bridge for the covalent attachment is designed so that it limits or does not permit an energy transfer of the excited state from the molecular switch to the square planar complex.

Figure 1:
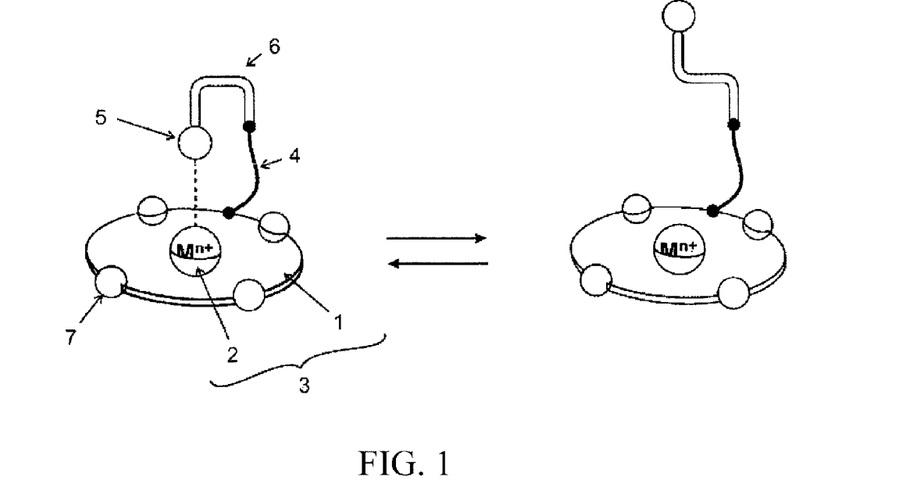

A schematic drawing of the principle is shown in FIG. 1.

In principle, all square planar nickel, cobalt, iron or manganese complexes are suitable that bear a switchable ligand that allows a reversible occupying of and removing again from one of the two axial coordination sites, and whose spin state can be specifically changed by association or dissociation of the axial ligand.

Ni (II) offers two different spin states depending on the coordination sphere. If n is the coordination number, $Ni^{24}$ has the diamagnetic low spin state (S=0) in square planar complexes (n=4), and always the paramagnetic high spin state (S=1) in square bipyramidal complexes (n=6). Square pyramidal complexes (n=5) can exhibit the high spin or the low spin state, depending on the nature of the ligand used. If two axial ligands are added to a square planar Ni(II) complex increasing the coordination number from 4 to 6, the spin state changes from low spin to high spin.

As chelate ligands for the square planar complex, ligands can be named that force a square planar configuration, preferably porphyrins, phthalocyanines, porphyrazines, naphthocya-nines, chlorins, bacteriochlorins, corrins, corroles and other tetrapyrroles and their hetero-analoga, as well as salens, glyoximes, triethylentetramines, cyclam (1.4,8.11-tetraazacyclotetradecane) and derivatives of 1.4,8.11-tetrathiocyclotetradecane.

Ligands with strong electron-donor properties can be named as axial ligands, in particular substituted pyridines, imidazoles, pyrrolidines, piperidines, pyrroles, pyrazines, triazoles, tetrazoles, alkyl amines, phosphines, arsines, thiols, thioethers and tetrahydrothiophene.

As photochromic systems, those systems are particularly suitable that undergo an isomerization on irradiation with light of a wavelength between 300 and 900 nm, particularly preferred are azobenzene, phenylazopyridine or azopyridine, thioindigo, hemithioindigo, spiropyrans, spiroindolizines, diarylethenes and fulgides.

The covalent attachment of the molecular switch to the square planar complex is provided by a suitable bridge. This is a unique advantage of the invention. The axial ligand is bound directly to the chelate ligand via covalent chemical bonds.

In principle, the constitution and the function of the switchable transition metal complex can be compared to a record player. The record turntable corresponds to the square planar chelate complex and the pickup arm is formed by the bridge (covalent attachment) and the photochromic system. The latter carries out the light-controlled movement of the pickup arm. The needle of the pickup atm is the lone electron pair of the axial ligand (see FIG. 1). It was found that a suitable design allows the combination of two or more of the functions mentioned above in one molecule. Thus, azopyridine as switchable molecule in the example molecule in FIG. 2 already comprises the needle (the lone electron pair of the pyridine nitrogen) and concomitantly mediates part of the covalent attachment via the phenyl ring. All of the molecular building blocks mentioned above must be geometrically adjusted to each other so that in one of the two switching states, the lone electron pair of the axial ligand is positioned perpendicular to the square planar complex and at a distance of about 1.8-2.4 Å to the metal ion (depending on the axial ligand, the metal ion and the oxidation state) and engages an axial coordination with the metal ion when the isomerization of the switchable molecule is induced by light. In the other switch state, the lone electron pair must have an angle different from 90° and a greater distance (>2.4 Å) and must not coordinate with the metal ion.

In case of porphyrin as square planar chelate ligand, there are two basic possibilities for a covalent attachment of the bridge: (a) in meso-position and (b) in β-position. In case of the phenylazopyridine as switchable ligand, there are three different regioisomers with the azo group in positions 2, 3 and 4 of the pyridine ring. For the 3-phenylazopyridine, in turn, there are 7 attachment possibilities for the bridge: on positions 2, 4, 5 and 6 of the pyridine ring and on positions 2, 3 and 4 of the phenyl ring. As a result, there is a plurality of combinational possibilities starting with porphyrin and azopyridine as basic building blocks. For each of these, a suitable bridge must be found that links porphyrin and azobenzene in such a way that an operational system is generated. For this purpose, the bridge essentially must meet two requirements: (a) it must be constructed geometrically so that it effects an axial coordination or decoordination, (b) it must be tuned electronically so that no direct, continuous conjugation of the switchable molecule with the square planar molecule is formed, as this affects the switching behavior. (c) it should have the fewest possible degrees of freedom (rotation around single bonds) in order to prevent a drifting away of the axial ligand. For example, in order to attach a nickel porphyrin in meso-position to the 3-phenylazopyridine in position 2 (ortho with regard to the azo group) of the phenyl ring, the bridge must comprise three $CH_2$ groups wherein these $CH_2$ groups can be replaced by, e.g., O or NH as a first approximation to facilitate the synthesizability. In this geometry, pyridine coordinates with nickel when the azo group is in the cis-position, and does not coordinate when the azo group is in the trans-position. In order to link a nickel 2.3-dihydro-porphyrin in position 2 with a 3-phenylazopyridine in position 2 (ortho with regard to the azo group) on the phenyl ring, a chain of three $CH_2$ groups is required ideally. Here, too, one or more of the $CH_2$ groups may be replaced by atoms or groups of similar geometry. Such a bridge would effect a coordination of the pyridine nitrogen when the azo group is in the trans-configuration and not in the cis-configuration.

Figure 2:
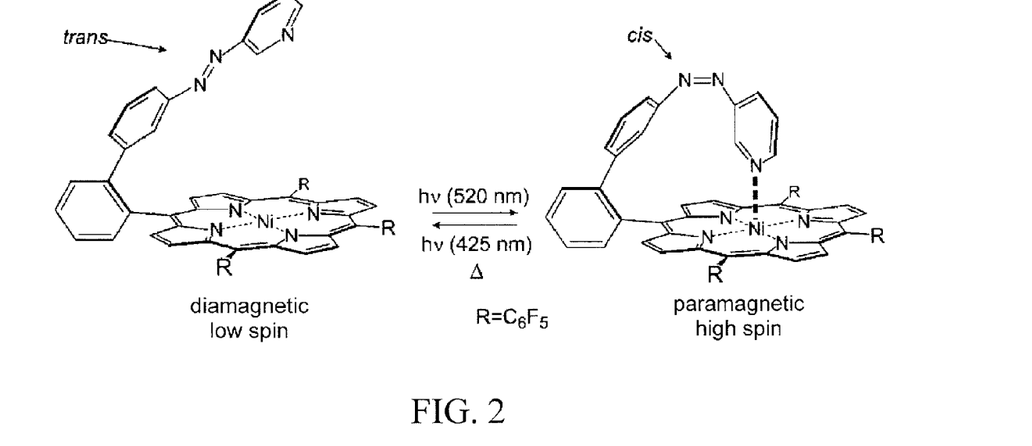

FIG. 2 shows as an example a Ni porphyrin complex of the invention, functionalized with azopyridine, that was prepared and whose switchability according to the principles stated above was demonstrated experimentally.

Figure 3A:
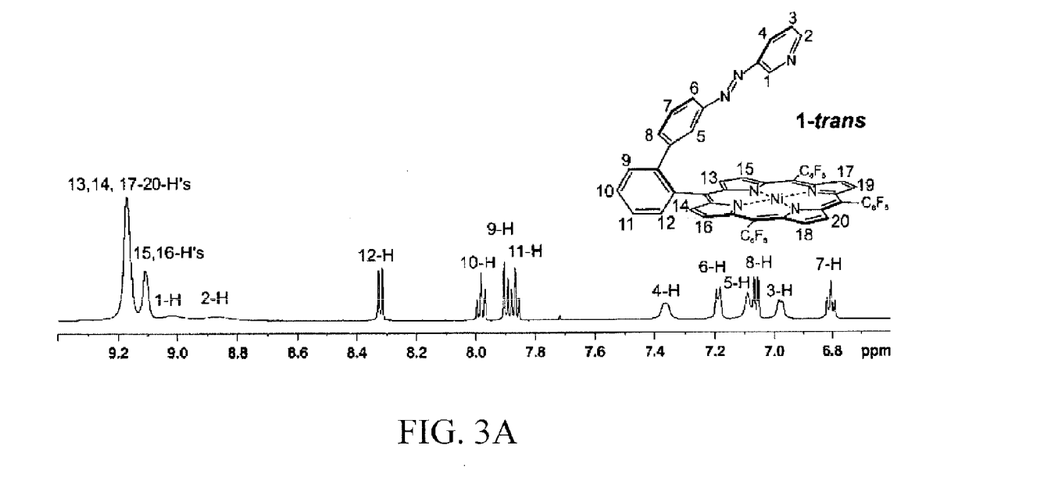
Figure 3B:
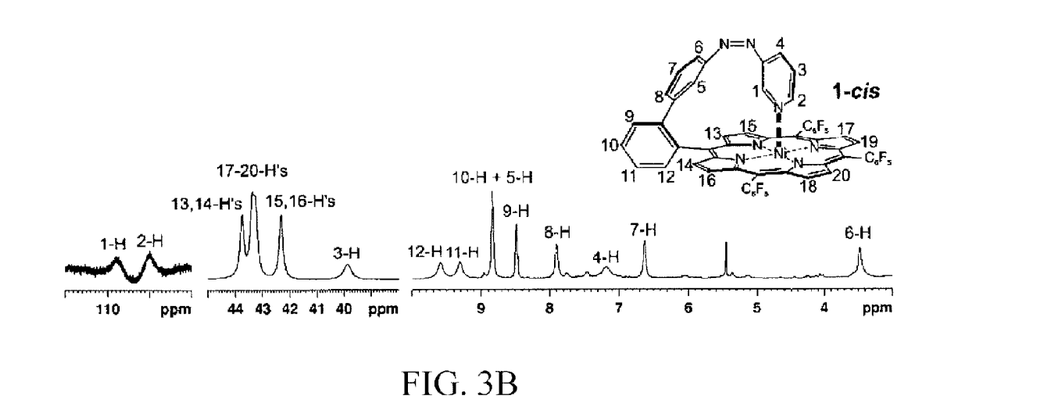

FIG. 3 shows the NMR spectra of both isomers of such a Ni porphyrin complex of the present invention functionalized with azopyridine. The transition from the trans- into the cis-state is accompanied by a strong downfield shift and broadening of the signals.

The principle of the switchable complexes of the present invention ("record-player complexes") can be observed in FIG. 1. By irradiation with light having a wavelength between and 520 nm or 330 nm or 380 nm, preferably 510 nm, the molecule rearranges at the azo functionality (—N=N—) from the trans-((E)-isomer) into the cis-((Z)-isomer). In the cis-configuration, the pyridine nitrogen with its lone electron pair occupies the axial coordination site. As a result, a transition occurs from the diamagnetic low spin state of the trans-configuration to a paramagnetic high spin state. Irradiation with light having a wavelength of 420-450 nm, preferably 425 nm, leads again to a change of the configuration of the azo functionality. The molecule is rearranged back into the cis-configuration, which results in a change of the spin state from the paramagnetic high spin state into the diamagnetic low spin state.

A specific advantage of the complexes according to the present invention is the possibility to use light with a frequency in the range of visible light for switching between the different states. These wavelengths are much more physiologically acceptable than light from the UV range, for example. Thus, it is possible to use such complexes for applications related to the human body as well.

Due to the extremely high absorbance of the cis-compound (epsilon=230 000 1 $mol^{-1}$ $cm^{-1}$, at 425 nm) and the high quantum yield (~15%), the switching of the invention of the complexes according to the invention is very sensitive in this wavelength range so that neither high intensities nor energies are required. For these reasons, the most important physical requirements for an application such as a light-switchable MRI contrast agent are met.

The switching operations on the compounds of the invention have proven to be extremely reversible. Even after more than 10.000 switching cycles, no side reactions or symptoms of fatigue are observed. This result is also found at room temperature and under air. The experiments with 10.000 switching cycles were carried out at 20° C. and under air.

The lifetime of the paramagnetic state of the complexes of the invention is very high. The half life of the paramagnetic state at room temperature (21° C.) is several months. The determination of the half life was carried out by NMR as well as UV spectroscopy.

A further advantage of the molecular switches according to the invention is that they are stable and switchable in solution as well.

This means, among others, that they can be directly injected into the blood flow as switchable contrast agents. The disadvantages of contrast agents that are only active in form of solids are thus avoided. These disadvantages are the inevitable encapsulation of the solids to protect them against dissolution on the one hand, and on the other hand the possible blockage of blood vessels due to the fact that the particles can only be introduced in a suspended form.

A specific advantage of the molecular switch of the invention therefore is the possibility to use it as switchable contrast agent for magnetic resonance imaging. The complexes of the invention are only effective as contrast agent in their paramagnetic state. Therefore, switchable contrast agents have the advantage that the signal-to-noise ratio can be improved by switching if images are recorded alternately with active and inactive contrast agent, which allows an elimination of the background by averaging.

The switchable contrast agent also allows the monitoring of the blood flow, which is impossible to do with a conventional contrast agent. This is carried out by irradiating a certain site of a blood vessel, switching on the contrast agent, and monitoring its distribution with several consecutive images. The switchable contrast agent also permits adjusting the switching frequency of the contrast agent to the heart rate, which allows the collection of images of the same phase of the movement and the merging of these to a static image.

One very advantageous application of the molecular switch of the invention which is stable in the paramagnetic state and also in solution is the contact-free manipulation of objects, which is explained in more detail below.

As early as in the 60 s, the magnetohydrostatic principle (also called magnetic Archimedes' principle) was proposed for separating ores (U. Andres. Magnetohydrodynamic and Magnetohydrostatix Methods of Mineral Separation; Wiley: New York, 1976). Recently, the same principle was proposed for determining the density of diamagnetic substances (K. A. Mirica, S. S. Shevkoplyas, S. T. Phillips, M. Gupta, G. M. Whitesides, J. Am. Chem. Soc. 2009, 131, 10049-10058). This requires a strong magnet for generating an inhomogeneous magnetic field whose gradient should be as parallel as possible to the gravitational acceleration (i.e. perpendicular to the surface of the earth), and whose vector is parallel to the gravity of the earth (i.e. the strength of the magnetic field B decreases from bottom to top). Into this inhomogeneous magnetic field, a paramagnetic liquid is introduced. This liquid can be a solution of a paramagnetic salt (e.g. $MnCl_2$, $FeCl_2$, $CoBr_2$, $NiSO_4$, $Dy_2(SO_4)_3$), or a suspension of a ferromagnetic material (e.g. magnetite ($Fe_3O_4$) or artificial ferrites (e.g. $Fe_3Y_5O_{12}$)). The diamagnetic samples are present in this liquid. Two different forces now affect the samples. 1. The gravitational force minus the buoyancy in the liquid, and 2. a magnetic force pointing in the direction of the decreasing magnetic field (i.e. opposed to the gravity). The gravitational force $F_{grav}$ is equal in all places and depends only on the density difference between liquid and sample.

$$F_{grav} = (\rho_p - \rho_m) V g$$

$\rho_p$: density of the sample
$\rho_m$: density of the medium
V: sample volume
g: gravitational constant The magnetic force depends on the strength of the magnetic field, of the magnetic field gradient and on the difference of the magnetic susceptibility of sample and solution.

$$F_{mag} = [(\chi_p - \chi_m)/\mu_0] V B_z dB_z/dz$$

$\chi_p$: magnetic susceptibility of the sample
$\chi_m$: magnetic susceptibility of the medium
$\mu_0$: magnetic permeability of free space
$B_z$: magnetic induction in z-direction (perpendicular to the surface of the earth)
$dB_z/dz$: magnetic field gradient in z-direction The magnetic force decreases with increasing distance to the magnet. If gravitational force and magnetic force are opposed to each other, there is a certain distance from the magnet where the sample is in equilibrium because both forces cancel each other out at this position. The sample then floats motionless in a position that, under constant outer parameters, depends only on the density and the magnetic susceptibility of the sample.

Figure 5A:
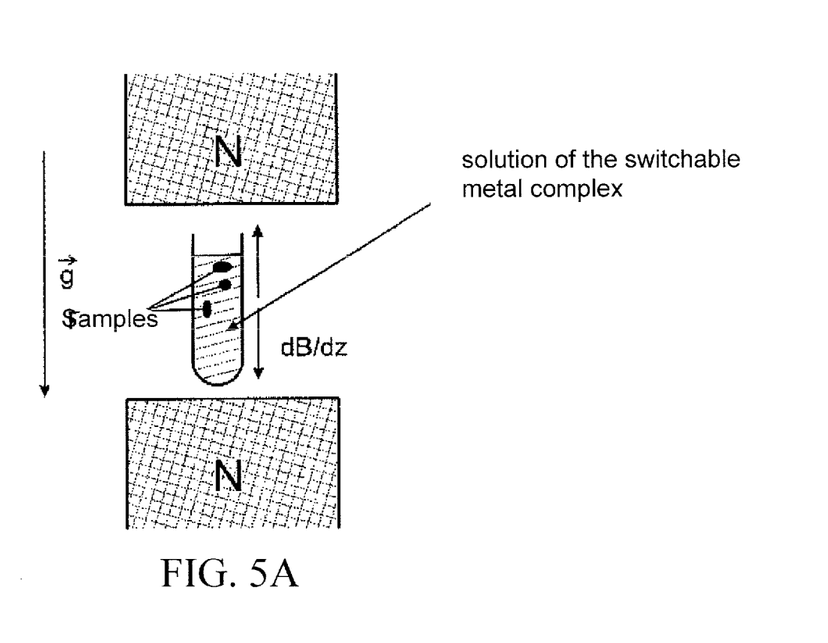
Figure 5B:
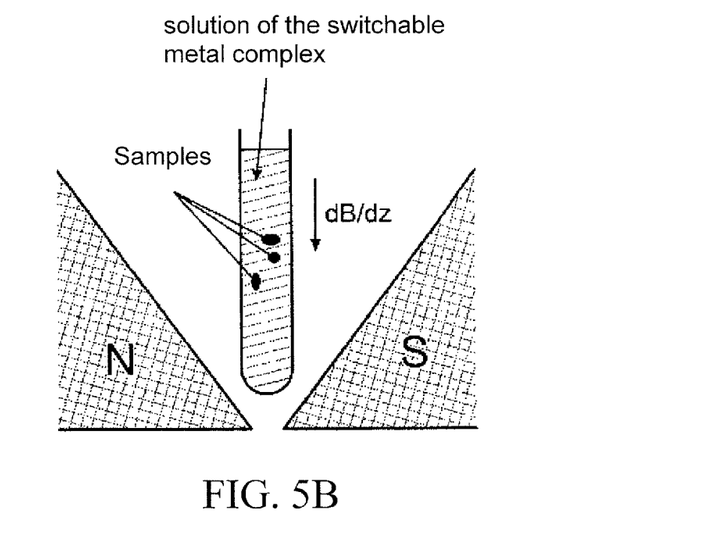
Figure 6A:
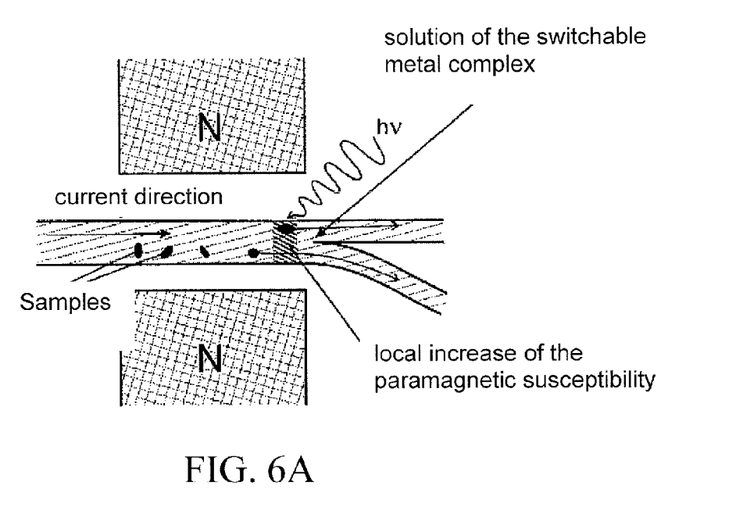
Figure 6B:
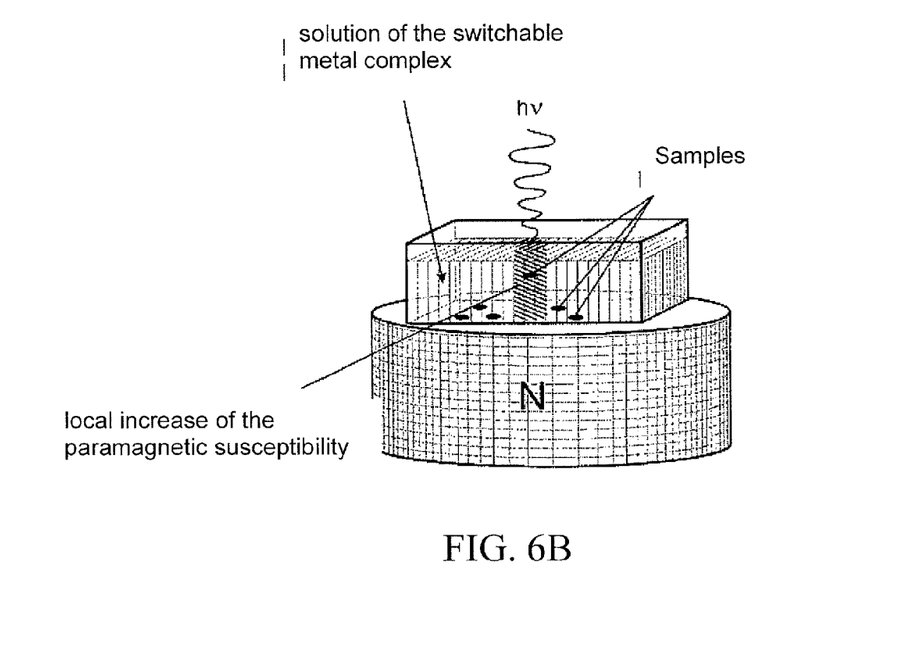

The actual design of such an installation is simple (see FIG. 5). The magnetic field gradient is generated, for example, by either placing two magnets according to a so-called anti-Helmholtz arrangement (like poles face each other vertically so that they repel each other, e.g. north pole faces north pole). This results in an essentially constant field gradient (the magnetic induction B decreases linearly from each magnet to the middle). Exactly between both magnets, the vertical component of B (in z-direction) is zero. Alternatively, both magnets are placed in an arrangement where north pole and south pole are placed horizontally to each other. The distance between both poles must be wedge-shaped (closer together at the bottom than at the top) (FIG. 5). In the simplest scenario, a single magnet is sufficient whose north or south pole point upwards (FIG. 6b). The inhomogeneous magnetic field can be generated either by strong permanent magnets (e.g. $Nd_2Fe_{14}B$ or $SmCo_5$ or $Sm_2Co_{17}$) or by electro magnets.

The novelty of our invention is that now the solution of the molecular switch of the invention is introduced into the homogeneous magnetic field instead of the solution of the paramagnetic salt or the suspension of paramagnetic particles. In contrast to a simple solution of a metal salt, the magnetic susceptibility of this solution now can be changed reversibly with light (e.g. by a laser with two different wavelengths) with a high spatial resolution. If the magnetic susceptibility in the environment of a certain sample is changed by irradiation with light, the magnetic force acting on the sample changes. The sample is either lifted if the paramagnetic susceptibility is increased (switching to the high spin state), or lowered (switching to the low spin state). Many practical applications are conceivable. For example, if a liquid flow comprising small objects such as bacteria or cells is passed in a tube through the magnetic field, it may be possible to sort out individual objects by a targeted irradiation with light that leads to a lifting or lowering of these objects which in turn guides them in a suitable manner into a branch (FIG. 6a)). Similarly, placing objects, e.g. for microscopic studies, or exactly positioning of microelectronic components can be carried out by using the contact-free manipulation by means of light. For this purpose, a vessel with the solution of the switchable metal complex of the invention is placed on the surface of the pole of a magnet. The strength of the magnetic field, the specific weight of the sample and of the solution must be adjusted so that the magnetic levitation is not sufficient to make the sample float ($F_{grav} > -F_{magn}$) if the metal complex is in the low spin state. By irradiation with light in the vicinity of a sample and by isomerization of the complex into the high spin state, the sample is lifted from the bottom of the vessel, moved sidewards by applying a horizontal magnetic field gradient and lowered again by switching back the metal complex into the low spin state (FIG. 6b)).

A further application of the molecular switch of the invention is in the field of optical storage media. Writing and erasing of information is effected here by switching the molecular switch after irradiation with light of the appropriate wavelength. In the case of the Ni porphyrin complexes functionalized with azopyridine as shown in FIG. 2, this wavelength is 520 nm or 425 nm, respectively. To read out the information, light of a wavelength is used that does not cause isomerization, i.e. a switching, but is absorbed by only one of the two isomers (cis or trans). In the case of the Ni porphyrin complexes functionalized with azopyridine as shown in FIG. 2, this wavelength is, e.g., 544 nm.

The preparation of the molecular switches of the invention is carried out following a multistep process.

1. In the simplest case, the photochromic system is prepared from the components 3-bromonitrobenzene and 3-aminopyridine. 3-Bromonitrobenzene with substituents in position 2, 4, 5 or 6 can be used as well. Instead of the bromo compound, the corresponding chloro and iodo compounds or other substituents that are suitable for the Suzuki coupling carried out in a later step (e.g. triflate) can also be used. Moreover, substituted aminopyridines can be used as well. In this case, electron-donating substituents in position 4 are advantageous. For the coupling of the components, 3-bromonitrobenzene (or a corresponding derivative) is firstly reduced with Zn to the corresponding hydroxylamine and oxidized with $FeCl_3$ to give the nitro-so compound, which is not isolated, but directly reacted with 3-aminopyridine (or a corresponding derivative) to yield the corresponding azo compound 3-((3-bromophenyl)diazenyl)pyridine (or the corresponding derivative).

2. In the next step, the bridge, which in the present case is only a meta-substituted phenyl ring, is attached to the azo compound. This is done by reacting the bromo-substituted azo compound (or the corresponding derivative) with 2-formylphenyl boronic acid utilizing a Suzuki coupling. The latter compound may also be substituted in position 3, 4, 5 or 6, electron-drawing substituents being of advantage. The product 2-(pyridine-3-ylazo)benzaldehyde or the corresponding derivative is then used as component for the following cyclization to assemble the porphyrin ring.

3. In the synthesis of the porphyrin ring, the following three components are required to have a ratio of 4:3:1:
   a) pyrrole or pyrrole substituted in position 3 or 4.
   b) pentafluorobenzaldehyde (A) or another benzaldehyde, preferably bearing electron drawing substituents.
   c) 2-(pyridine-3-ylazo)benzaldehyde (B) (4), which may be substituted in position 2, 4, 5 or 6 of the pyridine, preferably with an electron donating substituent in position 4 (e.g. 2-((4-methoxypyridine-3-yl)diazenyl)benzaldehyde). 2-(Pyridine-3-ylazo)benzaldehydes, which are substituted in position 2, 3, 4 or 5 of the phenyl ring with regard to the azo group, can be used as well. The ring bearing the formyl group may be substituted as well.

The components condense with each other under catalysis with acids or Lewis acids (mixed aldehyde type of the Adler method) giving a statistic mixture of mesa-substituted porphyrins (substitution pattern: $A_4$, $A_3B$, cis-$A_2B_2$, trans-$A_2B_2$, $AB_3$, $B_4$), the desired $A_3B$-porphyrin being the main product, provided that both aldehydes have the same reactivity. The yield of the desired product can be increased if the pentafluorobenzaldehyde is precondensed with pyrrole and isolated to yield the dipyrromethane 2. Utilizing two equivalents of the dipyrromethane 2 as building block together with one equivalent of each, pentafluorobenzaldehyde and 2-(pyridine-3-ylazo)benzaldehyde, only three products can form ($A_4$, $A_3B$, trans-$A_2B_2$). Therefore, the yield of the desired product is correspondingly higher and the separation of the product mixture by chromatography is facilitated.

4. First, a porphyrinogen is formed by the cyclization, and then oxidized by air, or more advantageously by DDQ or chloranil to give porphyrin.

5. The nickel porphyrin, which is the compound of the invention, is formed by reaction with a Ni(II) salt, e.g. nickel acetonylacetate.

Alternatively, the sequence of the C—C-coupling in the synthesis may be swapped. That is, the assembly of the porphyrin ring can be carried out first with two equivalents of dipyrromethane and one equivalent of each of pentafluorobenzaldehyde and 2-bromobenzaldehyde or another benzaldehyde that is suitable for the following Suzuki coupling and is substituted in position 2. Next, the bromo atom on the obtained porphyrin substituted with three pentafluorophenyl and one 2-bromophenyl group is exchanged with boronic acid, which is then reacted with 3-((3-bromophenyl)diazenyl)pyridine in a Suzuki coupling, or conversely, the bromo-substituted porphyrin can also be coupled with (3-(pyridine-3-yldiazenyl)phenyl)boronic acid. The introduction of the nickel ion into the porphyrin ring may also be carried out after the ring closure instead of in the last step.

Figure 4:
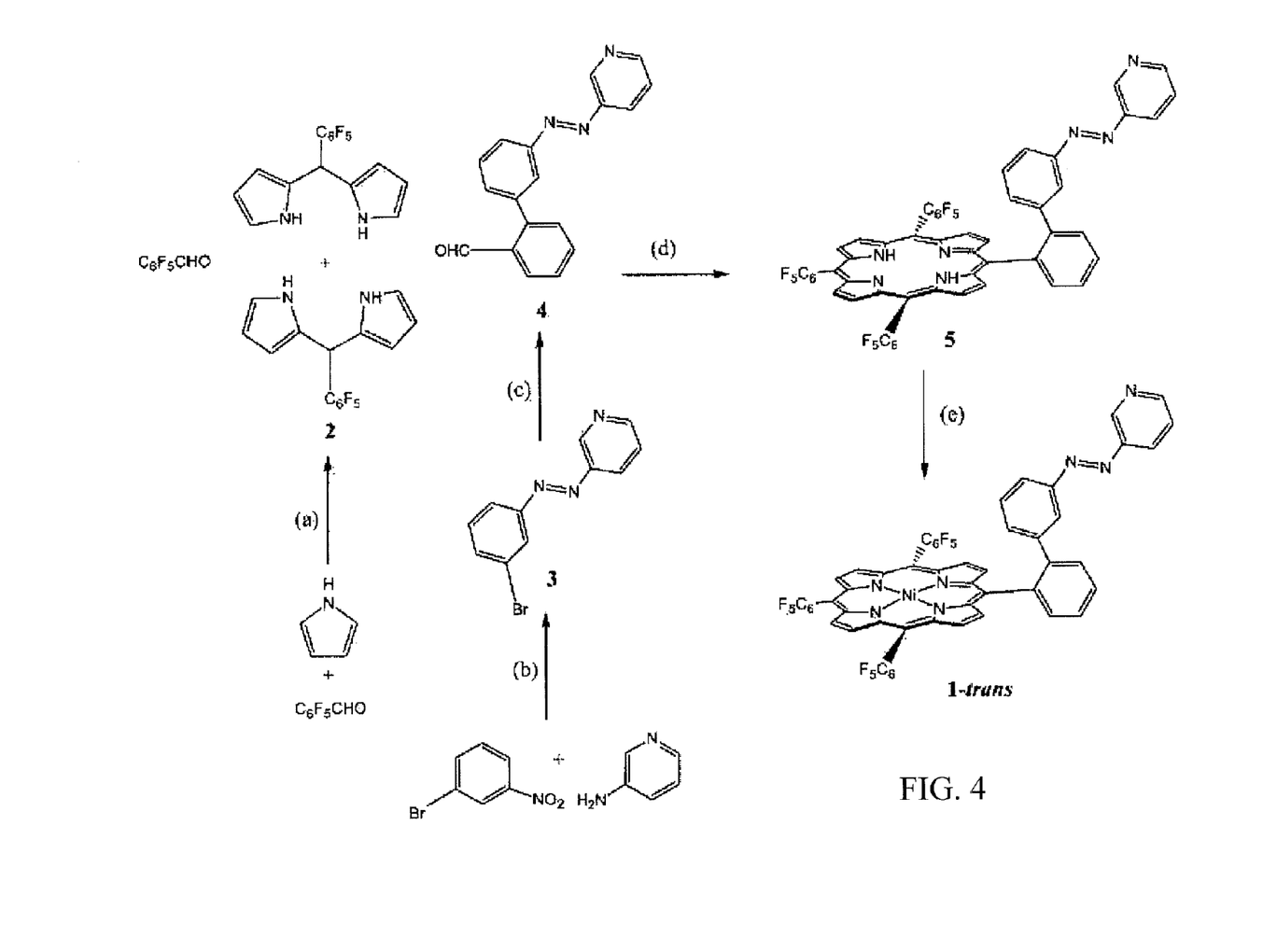

The synthesis of the complex of the invention is now explained by way of example and is not intended to limit the generality of the teachings. FIG. 4 shows the corresponding formulas.

b) Synthesis of 3:

To a stirred solution of 3-bromonitrobenzene (8.08 g, 40 mmol) in ethanol (150 mL), a solution of $NH_4Cl$ (3.21 g, 60 mmol) in 15 mL of water is added under a nitrogen atmosphere. The resulting mixture is heated to 40° C. to obtain a clear solution. To this solution, Zn powder (6.54 g, 100 mmol) is added slowly at room temperature for a period of 20 min, and stirring is continued for another 2 h. The reaction mixture is filtered and washed with ethanol and then with water. The combined, light yellow filtrate is then added dropwise to an ice-cold solution of $FeCl_3 \cdot 6H_2O$ (18 g, 66 mmol) in 200 mL $H_2O$ while stirring. A greenish yellow precipitate is formed, which is separated off by filtration and washed with water. The product is air dried for two days and this crude product (7.2 g, 38.70 mmol) is slowly added to a stirred, biphasic solution of 3-aminopyridine (3.57 g, 38 mmol) in toluene (30 mL) and 40% NaOH solution (20 mL) at 80° C. under a nitrogen atmosphere. The mixture is heated to reflux for 2.5 h. Then the reaction mixture is allowed to attain room temperature and is extracted with ethyl acetate (150 mL). The ethyl acetate extract is washed with water (2×100 mL), dried over anhydrous $Na_2SO_4$ and the solvent is removed under reduced pressure. The crude product is purified by flash chromatography on silica gel using ethyl acetate and cyclohexane (3:7) as the eluent to afford a pure orange red solid 3 (3.47 g, 13.24 mmol, 35%), $R_f$=0.53 (1:1 ethyl acetate and cyclohexane).

Mp.; 71-72° C.; IR(cm$^{-1}$): 3057 (w), 1570 (s), 1449 (m), 1422 (s), 812 (vs), 780 (vs), 696 (vs), 674 (vs), 616 (s), 547 (s), 533 (s), 480 (m); UV-vis (CHCl$_3$) ($\lambda_{max}$ in nm, abs. units): 319 (0.66), 242 (0.41); $^1$H NMR (CDCl$_3$, 500 MHz): δ=7.42 (t, J=8.0 Hz, 1H, H-8), 7.45 (ddd, J=8.0, 4.7, 0.7 Hz, 1H, H-2), 7.63 (ddd, J=7.9, 1.95, 1.0 Hz, 11-7), 7.91 (ddd, J=8.0, 1.85, 1.0 Hz, 11-9), 8.08 (t, J=1.85 Hz, 1H-1, H-11), 8.13 (ddd, J=8.20, 2.34, 1.6 Hz, 1H, H-3), 8.72 (dd, J=4.72, 1.6 Hz, 1H, H-1), 9.20 (dd, J=2.4, 0.5 Hz, 1H, H-5); $^{13}$C NMR (CDCl$_3$, 125 MHz) δ=123.14 (C-9), 123.24 (C-10), 124.03 (C-2), 124.87 (C-11), 126.97 (C-3), 130.57 (C-8), 134.35 (C-7), 147.55 (C-4), 147.61 (C-5), 152.24 (C-1), 153.31 (C-6) ppm. MS [m/z (%)] 262.0 (100), 261.0 (49), 260.0 (97), 259.0 (32); Elemental analysis: Calc. for $C_{11}H_8BrN_3$: C, 50.41; H, 3.08; N, 16.03; found: C, 50.50; H, 3.07; N, 16.01.

c) Synthesis of 4:

To a stirred solution of 3 (1.00 g, 3.81 mmol) in dry toluene (30 mL) under a nitrogen atmosphere, 2-formylphenyl boronic acid (630 mg, 4.2 mmol), ethanol (10 mL), $K_2CO_3$ (2 mL, 2 M solution in water) and Pd(PPh$_3$)$_4$ (60 mg) are added successively. Then the solution is stirred vigorously and heated to 90° C. The progress of the reaction was monitored by thin layer chromatography. After heating for 16 hours (oil bath), the mixture was cooled down to room temperature and extracted with ethyl acetate (100 mL). The organic layer is separated and washed with water (2×50 mL), dried over anhydrous $Na_2SO_4$ and concentrated in vacuo. The dark orange residue was purified by flash chromatography on silica gel by using ethyl acetate and hexane (3:7) as eluents to afford compound 4 as an orange-red solid (1.04 g, 3.61 mmol, 95%), $R_f$=0.438 (40% ethyl acetate and cyclohexane).

Mp. 97-98° C.: IR (cm$^{-1}$): 3045 (w), 2862 (w), 1685 (s), 1589 (s), 1190 (s), 815 (vs), 758 (vs), 698 (vs), 647 (s), 614 (s), 510 (s); UV-vis (CHCl$_3$) ($\lambda_{max}$ in nm, abs. units): 320 (0.83), 2.57 (0.62), 242 (0.67);

$^1$H NMR (CDCl$_3$, 500 MHz): δ=7.47 (dd, J=8.0, 4.7 Hz, 1H, H-2), 7.52-7.58 (m, 3H, H-9, H-15 and H-17), 7.66 (t, J=8.0 Hz, 1H, H-8), 7.69 (td, J=7.50, 1.4 Hz, 1H, H-16), 7.98 (t, J=2.0 Hz, 1H, H-11), 8.04 (dt, J=8.0, 1.6 Hz, 1H, H-7), 8.07 (dd, J=8.0, 1.5 Hz, 1H, H-14), 8.17 (dt, J=8.0, 2.0 Hz, 1H, H-3), 8.73 (dd, J=5.0, 1.5 Hz, 1H, H-1), 9.22 (d, J=2.30 Hz, 1H, C-5), 10.06 (d, J=0.6 Hz, 1H, H-18); $^{13}$C NMR (CDCl$_3$, 125 MHz) δ=123.09 (C-7), 124.04 (C-2), 124.07 (C-11), 127.01 (C-3), 127.95 (C-14), 128.31 (C-9). 129.31 (C-8), 130.82 (C-15), 133.10 (C-17), 133.73 (C-13), 133.78 (C-16), 139.02 (C-10), 144.80 (C-12), 147.46 (C-5), 157.74 (C-4), 152.00 (C-1), 152.33 (C-6), 191.45 (C-18) ppm.

MS [m/z (%)] 277.1 (75), 278.1 (42), 287.1 (100); Elemental analysis: Calc. for $C_{15}H_{13}N_3O$: C, 75.25; H, 4.56; N, 14.63; found: C, 75.24; H, 4.75; N, 14.79.

d) Synthesis of the Metal-Free Porphyrin 5:

In a 500 mL two-neck round-bottom flask, $CH_2Cl_2$ (425 mL), dipyrromethane 2 (2.15 g, 6.8 mmol), aldehyde 4 (0.97 g, 3.3 mmol) and pentafluorobenzaldehyde (0.66 g, 3.3 mmol) are added successively, and the flask is wrapped with aluminum foil. The mixture is vigorously stirred and purged with nitrogen for 15 min at room temperature. Then $BF_3 \cdot OEt_2$ (0.98 g, 6.9 mmol) is added by means of a syringe. The reaction mixture is stirred for another 14 h at room temperature. Then p-Chloranil (1.74 g, 7.1 mmol) is added in one portion and the mixture is refluxed for 7 h. The reaction mixture is cooled to room temperature, and Et$_3$N (1 mL, 7.2 mmol) is added and stirring is continued for additional 30 minutes. Finally, the solvent is removed to dryness. The dark green reaction product is purified by repeated flash chromatography on silica gel using $CH_2Cl_2$ as eluent finally to afford the desired product 5 as purple solid (152 mg, 0.143 mmol, 4.2%). $R_f$=0.46 (2.5% ethyl acetate and $CH_2Cl_2$).

IR (pure, cm$^{-1}$, intensity): 3318 (vw), 1723 (m), 1516 (s), 1494 (vs), 1261 (m), 1041 (s), 985 (vs), 917 (vs), 802 (s), 756 (vs), 701 (s);

UV-vis (CHCl$_3$) ($\lambda_{max}$ in nm, abs. units): 586 (0.02), 512 (0.06), 418 (0.61), 347 (0.10); $^1$H NMR (CDCl$_3$, TMS, 500 MHz): δ=2.92 (s, 2H, —NH), 6.50-6.53 (t, J=7.9 Hz, 1H, 7-H), 7.00-7.02 (dm, J=8.0 and 1.1 Hz, 1H, 8-H), 7.06-7.08 (dm, J=8.0 and 1.1 Hz, 114, 6-H), 7.19-7.22 (dd, J=5.0, 3.4 Hz, 1H, 3-H), 7.47-7.49 (dm, J=8.1 and 2.1 Hz, 1H, 4-H), 7.75 (t, 1H J=1.9 Hz, 5-H), 7.76-7.80 (m, 1H, 11-H), 7.93-7.96 (m, 2H, 10-H and 9-H), 8.18-8.20 (dm, J=7.5 and 1.1 Hz, 1H, 12-H), 8.51-8.52 (dd, J=5.0 and 1.7 Hz, 1H, 2-H), 8.71-8.75 (m, 3H, 1-H, 13-H and 14-H), 8.81-8.86 (m, 4H, 17-H, 18-H, 19-H and 20-H), 8.94-8.97 (d, J=4.8 Hz, 2H, 15-H, 16-H) ppm;

$^{13}$C NMR (CDCl$_3$, 125 MHz) δ=151.48 (C-5a), 150.53 (C-2), 147.41 (C-4a), 147.41 and 145.52 (6C, ortho F-C of C6F5 (X+Y+Z)), 145.86 (C-1), 143.84 (C-9a), 143.21 and 141.13 (3C, para F-C of C6F5 (X+Y+Z)), 142.15 (C-8a), 139.27 (C-12a), 138.55 and 136.54 (6C, meta F-C of C6F5 (X+Y+Z)), 135.72 (C-12), 132.55 (C-8), 135.00-130.00 (br, 13-20, 13a-20a), 129.67 (C-10), 129.44 (C-9), 128.38 (C-7), 127.47 (C-4), 126.26 (C-11), 123.89 (C-5), 123.86 (C-3), 121.73 (C-A), 121.31 (C-6), 116.00-115.00 (br, 3C, q-C of C6F5 (X, Y, Z)), 102.94 (C-B and C-D), 102.00 (C-C) ppm;

$^{19}$F NMR (CDCl$_3$, 470 MHz): δ=−136.57 to −136.69 (m, 6-o-F of X, Y and Z), −151.63, −151.67, −151.72 and −151.76 (q, J=21 Hz, 3-p-F of X, Y and Z), −161.48-−161.68 (m, 4-m-F of X, Y and Z);

MS [EI, m/z] 1065.0 (100), 1045.7 (8%), 959.0 (10%), 532.8 (20%).

e) Synthesis of the Ni Porphyrin (1):

To a stirred solution of porphyrin 5 (65 mg, 0.0610 mmol) in toluene (20 mL), Ni(acac)$_2$ (230 mg, 0.785 mmol) is added under a nitrogen atmosphere. The mixture is refluxed for 5 days and the progress of the reaction is monitored by thin layer chromatography. Then the reaction mixture is cooled to room temperature and the solvent is evaporated to dryness under vacuum. The crude product is purified by flash chromatography on silica gel using 1% ethyl acetate in $CH_2Cl_2$ as eluent to afford a purple product (red solution) (50 mg, 0.0446 mmol, 73%); $R_f$=0.46 (2.5% EtOAc and $CH_2Cl_2$). Upon separation on a thin layer chromatography plate, two spots corresponding to 1-cis and 1-trans, respectively, can be observed upon standing in light. (Eluent: 10% ethyl acetate in $CH_2Cl_2$).

IR (pure, $cm^{-1}$, intensity): 1517 (s), 1485 (vs), 1345 (m), 1059 (m), 985 (vs), 957 (vs), 937 (s), 800 (m), 761 (vs), 701 (s);

UV-vis (in $CH_3CN$, 20° C.) $\lambda_{max}$ [nm], ($\epsilon/10^3$ [$L \cdot mol^{-1} \cdot cm^{-1}$]): 1-trans 323 (28.1), 406 (170.6), 524 (12.9), 557 (8.7); 1-cis 321 (15.5), 421 (228.9), 544 (12.3);

$^1H$ NMR ($CH_3CN$, 600 MHz): 1-trans δ=6.78-6.80 (t, J=7.6 Hz, 1H, 11-7), 6.96-6.97 (br, d, J=7.0 Hz, 1H, H=3), 7.04-7.05 (d, J=7.9 Hz, 11-1, H-R), 7.07 (br, 1H, 7.17-7.18 (d, J=7.6 Hz, 1H, H-6), 7.34 (br, 1H, H-4), 7.84-7.86 (dt, J=7.9 and 1.1 Hz, 11-1, H-11), 7.87-7.89 (dd, J=7.9 and 1.1 Hz 1H, H-9), 7.95-7.98 (dt, J=7.9 and 1.1 Hz, 1H, H-10), 8.30-8.31 (d, J=7.6 Hz, 1H, 14-12), 8.85 (br, 1H, H-2), 9.00 (br, 1H, H-1), 9.09 (br, 2H, H-15 and H-16), 9.16 (br, 6H, H-13, H-14, and H-17-20) ppm;

1-cis δ=3.47 (br, 1H, H-6), 6.63 (s, 1H, 11-7), 7.18 (br, 1H, H-4), 7.90 (s, 1H, H-8), 8.48 (s, 1H, H-9), 8.83 (br, 2H, H-10 and H-5), 9.31 (br, 1H, H-11), 9.60 (br, 1H, H-12), 39.86 (br, 1H, H-3), 42.32 (br, 214, H-15, 16), 43.28 and 43.35 (br, 4H, H-17-20), 43.75 (br, 2H, H-13, 14), 100.08 (br, 111, 11-2), 107.88 (br, 1H, H-1) ppm;

MS [EI, m/z] 1122.1 (60%), 1121.2 (100%), 1015.1 (10%), 560.7 (8%);

In order to demonstrate the reversibility of the switching operation, the following experiment was carried out:

To investigate the long-term stability and the reversibility of the Ni porphyrin functionalized with azopyridine with regard to switching with light, both an NMR tube and a UV cuvette were irradiated alternately with light having the wavelength of 500 nm and 435 nm. The NMR tube contained 0.5 ml of a 50 μm solution of the porphyrin 1 in $CD_3CN$ and the UV cuvette 3 ml of a 5 μm solution of the porphyrin 1 in $CH_3CN$. Light sources were an LED with a peak emission at 500 nm and a luminous intensity of 44 lm and an LED with a peak emission at 435 nm and 35 m lm. The irradiation was carried out alternately at 500 nm at a distance of 1 cm for 90 s and at 435 nm at a distance of 4 cm for 30 s. On irradiation with 500 nm, 50% of the molecules were switched into the cis-configuration after 90 s (50% trans), and on irradiation with 435 nm, 90% trans and 10% cis-compound were formed after 30 s. Neither NMR nor UV spectroscopy revealed the presence of any by-products or a decreasing switchability after more than 10.000 switching cycles.

Irradiating the Ni porphyrin functionalized with azopyridine for any period of time at 500 nm does not afford more than 65% of the cis-compound (photostationary equilibrium). Irradiation at 435 nm affords (if done long enough) 100% trans. Here, the photostationary equilibrium is completely on the trans-side.

LIST OF REFERENCE NUMBERS FOR FIG. 1

1 chelate ligand
2 transition metal ion
3 square planar or square bipyramidal transition metal complex
4 bridge
5 axial ligand
6 photochromic system
7 coordination site on the chelate ligand

The invention claimed is:

1. A photosensitive molecular switch, having
a chelate ligand,
a metal ion coordinatively bound to the chelate ligand, the metal ion being selected from the group of metal ions consisting of $Mn^{2+}$, $Mn^{3+}$, $Fe^{2+}$, $Fe^{3+}$, $Co^{2+}$ and $Ni^{2+}$,
a photochromic system that is covalently bound to the chelate ligand and can be isomerized by irradiation, this system being coordinatively bound to the metal ion in one configuration and not bound to the metal ion in the other configuration, wherein the photochromic system is azobenzene, phenyazopyridine, azopyridine, thioindigo, hemithioindigo, spiroindolizine, diarylethene or fulgide.

2. The photosensitive molecular switch according to claim 1, characterized in that a change of the magnetic state occurs by said isomerization of the photochromic system.

3. The photosensitive molecular switch according to claim 1, characterized in that the chelate ligand is selected from the group of ligands consisting of porphyrin, phthalocyanine, porphyrazine, naphthocyanine, chlorin, bacteriochlorin, corrin, corrole, salen, glyoxime, triethylenetramine, cyclam (1.4,8.11-tetraazacyclotetradecane) and derivatives of 1.4,8.11-tetrathiocyclotetradecane.

4. The photosensitive molecular switch according to claim 1, characterized in that the distance between the metal ion and the photochromic system is shorter than 2.4 Å in one configuration and greater than 2.4 Å in the other configuration.

5. The photosensitive molecular switch according to claim 1, characterized in that the photochromic system can be isomerized by irradiation with light having a wavelength of 300 to 900 nm.

6. A fluid, comprising a plurality of single molecules of the photosensitive molecular switch according to claim 1 in a solution.

7. A method, for light-controlled manipulation of an object comprising providing the object, applying a magnetic field to the object, and applying electromagnetic radiation to the object, wherein the object includes or is attached to a photosensitive molecular switch according to claim 1.

8. A contrast agent for magnetic resonance imaging, having a photosensitive molecular switch according to claim 1.

9. A storage medium for storing data, the storage medium having a photosensitive molecular switch according to claim 1.

10. The photosensitive molecular switch according to claim 2, characterized in that the chelate ligand is selected from the group of ligands consisting of porphyrin, phthalocyanine, porphyrazine, naphthocyanine, chlorin, bacteriochlorin, corrin, corrole, salen, glyoxime, triethylenetramine, cyclam (1.4,8.11-tetraazacyclotetradecane) and derivatives of 1.4,8.11-tetrathiocyclotetradecane.

11. The photosensitive molecular switch according to claim 2, characterized in that the distance between the metal ion and the photochromic system is shorter than 2.4 Å in one configuration and greater than 2.4 Å in the other configuration.

12. The photosensitive molecular switch according to claim 2, characterized in that the photochromic system can be isomerized by irradiation with light having a wavelength of 300 to 900 nm.

13. The photosensitive molecular switch according to claim 4, characterized in that the chelate ligand is selected from the group of ligands consisting of porphyrin, phthalocyanine, porphyrazine, naphthocyanine, chlorin, bacteriochlorin, corrin, corrole, salen, glyoxime, triethylenetetramine, cyclam (1.4,8.11-tetraazacyclotetradecane) and derivatives of 1.4,8.11-tetrathiocyclotetradecane.

14. The photosensitive molecular switch according to claim 4, characterized in that the photochromic system can be isomerized by irradiation with light having a wavelength of 300 to 900 nm.

* * * * *

UNITED STATES PATENT AND TRADEMARK OFFICE
CERTIFICATE OF CORRECTION

PATENT NO. : 9,786,420 B2
APPLICATION NO. : 13/817368
DATED : October 10, 2017
INVENTOR(S) : Rainer Herges et al.

It is certified that error appears in the above-identified patent and that said Letters Patent is hereby corrected as shown below:

Column 2,
Line 2, "Einzalmolekalen" should read -- Einzelmolekülen --.
Line 62, "(e.g. for $FP^{2+}$)" should read -- (e.g. for $Fe^{2+}$) --.

Column 3,
Line 17, "number, $Ni^{24}$" should read -- number, $Ni^{2+}$ --.
Line 29, "naphthocya-nines," should read -- naphthocyanines, --.
Line 30, "hetero-analoga," should read -- heteroanaloga, --.

Column 4,
Line 58, "between and 520 nm" should read -- between 500 and 520 nm --.

Column 5,
Line 67, "Magnetohydrostatix" should read -- Magnetohydrostatic --.

Column 6,
Line 36, "peimeability" should read -- permeability --.

Column 8,
Line 23, "mesa-substituted" should read -- meso-substituted --.

Column 9,
Line 26, "11-7)," should read -- H-7), --.
Line 27, "J=1.85 Hz, 1H-1, H-11)," should read -- $J$=1.85 Hz, 1H, H-11), --.
Line 57, "2.57" should read -- 257 --.

Column 10,
Line 5, "$C_{15}H_{13}N_3O$:" should read -- $C_{18}H_{13}N_3O$: --.
Line 31, "δ=2.92" should read -- δ= -2.92 --.
Line 33, "1.1 Hz, 114," should read -- 1.1 Hz, 1H, --.

Signed and Sealed this
Third Day of July, 2018

Andrei Iancu
*Director of the United States Patent and Trademark Office*

CERTIFICATE OF CORRECTION (continued)
U.S. Pat. No. 9,786,420 B2

Column 11,
Line 13, "7.9 Hz, 11-1, H-R)," should read -- 7.9 Hz, 1H, H-8), --.
Line 13, "(br, 1H, 7.17-" should read -- (br, 1H, H-5), 7.17- --.
Line 15, "1.1 Hz, 11-1," should read -- 1.1 Hz, 1H, --.
Line 18, "1H, 14-12)," should read -- 1H, H-12), --.
Line 21, "(s, 1H, 11-7)," should read -- (s, 1H, H-7), --.
Line 24, "(br, 214," should read -- (br, 2H, --.
Line 26, "(br, 111, 11-2)," should read -- (br, 1H, H-2), --.